US011224409B2

(12) United States Patent
Greenleaf et al.

(10) Patent No.: US 11,224,409 B2
(45) Date of Patent: Jan. 18, 2022

(54) SHEAR WAVE GROUP VELOCITY ESTIMATION USING SPATIOTEMPORAL PEAKS AND AMPLITUDE THRESHOLDING

(71) Applicant: Mayo Foundation for Medical Education and Research, Rochester, MN (US)

(72) Inventors: James F. Greenleaf, Rochester, MN (US); Carolina Amador Carrascal, Rochester, MN (US); Shigao Chen, Rochester, MN (US); Matthew W. Urban, Rochester, MN (US); Armando Manduca, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 469 days.

(21) Appl. No.: 16/085,248

(22) PCT Filed: Mar. 14, 2017

(86) PCT No.: PCT/US2017/022221
§ 371 (c)(1),
(2) Date: Sep. 14, 2018

(87) PCT Pub. No.: WO2017/160783
PCT Pub. Date: Sep. 21, 2017

(65) Prior Publication Data
US 2019/0076126 A1 Mar. 14, 2019

Related U.S. Application Data

(60) Provisional application No. 62/307,764, filed on Mar. 14, 2016.

(51) Int. Cl.
*A61B 8/08* (2006.01)
*A61B 8/00* (2006.01)
(Continued)

(52) U.S. Cl.
CPC .............. *A61B 8/485* (2013.01); *A61B 8/463* (2013.01); *A61B 8/5207* (2013.01);
(Continued)

(58) Field of Classification Search
CPC ....... A61B 8/485; A61B 8/463; A61B 8/5207; A61B 8/5223; A61B 5/055; G01S 7/52042
See application file for complete search history.

(56) References Cited

U.S. PATENT DOCUMENTS 8,118,744 B2   2/2012  Palmeri
8,187,187 B2   5/2012  Fan
(Continued)

FOREIGN PATENT DOCUMENTS

DE   102013002065 A1   8/2013
WO   2015/009339 A1    1/2015

OTHER PUBLICATIONS

Engel, Aaron J. and Bashford, Gregory R., "A New Method for Shear Wave Speed Estimation in Shear Wave, Elastography" (2015). Biomedical Imaging and Biosignal Analysis Laboratory. 24. (Year: 2015).*
(Continued)

*Primary Examiner* — Amelie R Davis
*Assistant Examiner* — John Denny Li
(74) *Attorney, Agent, or Firm* — Quarles & Brady LLP

(57) ABSTRACT

Described here are systems and methods for estimating shear wave velocity from data acquired with a shear wave elastography system. More particularly, the systems and methods described here implement a spatiotemporal time-to-peak algorithm that searches for the times at which shear wave motion is at a maximum while also searching for the lateral locations at which shear wave motion is at a maximum. Motion can include displacement, velocity, or accel-
(Continued)

eration caused by propagating shear waves. A fitting procedure (e.g., a linear fit) is performed on a combined set of these temporal peaks and spatial peaks to estimate the shear wave velocity, from which mechanical properties can be computed. Motion amplitude thresholding can also be used to increase the number of points for the fitting.

35 Claims, 10 Drawing Sheets

(51) Int. Cl.
G01S 7/52 (2006.01)
A61B 5/055 (2006.01)
(52) U.S. Cl.
CPC ........ *A61B 8/5223* (2013.01); *G01S 7/52042* (2013.01); *A61B 5/055* (2013.01)

(56) References Cited

U.S. PATENT DOCUMENTS

| | | | | |
|---|---|---|---|---|
| 2004/0210135 | A1* | 10/2004 | Hynynen | A61B 8/54 600/439 |
| 2005/0165519 | A1* | 7/2005 | Ariyur | G05B 23/0232 702/190 |
| 2008/0249408 | A1* | 10/2008 | Palmeri | A61B 8/485 600/438 |
| 2013/0218012 | A1* | 8/2013 | Specht | G01S 15/8929 600/438 |
| 2013/0317362 | A1* | 11/2013 | Shi | A61B 5/0051 600/438 |
| 2015/0216507 | A1 | 8/2015 | Greenleaf | |
| 2015/0265249 | A1 | 9/2015 | Urban | |
| 2016/0183926 | A1* | 6/2016 | Asami | A61B 8/5207 600/438 |

OTHER PUBLICATIONS

Amador, C. et al, "Effects of phase aberration on acoustic radiation force-based shear wave generation," in Ultrasonics Symposium (IUS), 2014 IEEE International, 2014, pp. 2316-2319.
Bavu, E. et al, "Noninvasive In Vivo Liver Fibrosis Evaluation Using Supersonic Shear Imaging: A Clinical Study on 113 Hepatitis C Virus Patients," Ultrasound in Medicine & Biology, vol. 37, pp. 1361-1373, 2011.
Bercoff, J. et al. "Supersonic shear imaging: a new technique for soft tissue elasticity mapping." IEEE transactions on ultrasonics, ferroelectrics, and frequency control 51.4 (2004): 396-409.
Chen, S. et al, "Assessment of Liver Viscoelasticity by Using Shear Waves Induced by Ultrasound Radiation Force," Radiology, vol. 266, 2013.
European Patent Office, Extended European Search Report and Search Opinion for application 17767299.5, dated Oct. 31, 2019.
Ferraioli, G. et al, "WFUMB Guidelines and Recommendations for Clinical Use of Ultrasound Elastography: Part 3 Liver," Ultrasound in Medicine & Biology, vol. 41, pp. 1161-1179, 2015.
Fierbinteanu-Braticevici, C. et al, "Acoustic radiation force imaging sonoelastography for noninvasive staging of liver fibrosis," World Journal of Gastroenterology, vol. 15, pp. 5525-5532, Nov. 2009.
Gheonea, D. I. et al, "Real-time sono-elastography in the diagnosis of diffuse liver diseases," World Journal of Gastroenterology : WJG, vol. 16, pp. 1720-1726, 2010.
Goertz, R.S. et al, "Impact of Food Intake, Ultrasound Transducer, Breathing Maneuvers and Body Position on Acoustic Radiation Force Impulse (ARFI) Elastometry of the Liver," Ultraschall in Med, vol. 33, pp. 380-385, 07.08.2012 2012.
Hall, T.J. et al, "RSNA/QIBA: Shear wave speed as a biomarker for liver fibrosis staging," in Ultrasonics Symposium (IUS), 2013 IEEE International, 2013, pp. 397-400.

Hamhaber, U., et al. "Three-dimensional analysis of shear wave propagation observed by in vivo magnetic resonance elastography of the brain." Acta Biomaterialia 3.1 (2007): 127-137.
Joyce M. et al, "Shear wave speed recovery in transient elastography and supersonic imaging using propagating fronts," Inverse Problems, vol. 22, p. 681, 2006.
Kirk, G. D. et al, "Assessment of Liver Fibrosis by Transient Elastography in Persons with Hepatitis C Virus Infection or HIV-Hepatitis C Virus Coinfection," Clinical Infectious Diseases, vol. 48, pp. 963-972, Apr. 1, 2009 2009.
Knutsson, H. et al, "Local multiscale frequency and bandwidth estimation," in Image Processing, 1994. Proceedings. ICIP-94., IEEE International Conference, 1994, pp. 36-40 vol. 1.
McAleavey, S. et al, "Shear Modulus Imaging with Spatially Modulated Ultrasound Radiation Force," Ultrasonic Imaging, vol. 31, pp. 217-234, 2009.
McLaughlin J. et al, "Shear wave speed recovery in transient elastography and supersonic imaging using propagating fronts," Inverse Problems, vol. 22, p. 681, 2006.
Montaldo, G. et al, "Coherent Plane-Wave Compounding for Very High Frame Rate Ultrasonography and Transient Elastography," IEEE Transactions on Ultrasonics Ferroelectrics and Frequency Control, vol. 56, pp. 489-506, Mar. 2009.
Muthupillai, R. et al, "Magnetic resonance elastography by direct visualization of acoustic strain waves," Science, vol. 269, pp. 1854-1857, 1995.
Nierhoff, J. et al, "The efficiency of acoustic radiation force impulse imaging for the staging of liver fibrosis: a meta-analysis," European Radiology, vol. 23, pp. 3040-3053, Nov. 1, 2013 2013.
Nightingale, K. et al, "Acoustic radiation force impulse imaging: In vivo demonstration of clinical feasibility," Ultrasound in Medicine and Biology, vol. 28, pp. 227-235, Feb. 2002.
Oliphant, T.E. et al, "Complex-valued stiffness reconstruction for magnetic resonance elastography by algebraic inversion of the differential equation," Magnetic Resonance in Medicine, vol. 45, pp. 299-310, Feb. 2001.
Ophir, J. et al, "Elastography: A quantitative method for imaging the elasticity of biological tissues," Ultrasonic Imaging, vol. 13, pp. 111-134, 1991.
Palmeri, M. et al "RSNA QIBA ultrasound shear wave speed Phase II phantom study in viscoelastic media," in Ultrasonics Symposium (IUS), 2015 IEEE International, 2015, pp. 1-4.
Palmeri, M. L. et al , "Quantifying hepatic shear modulus in vivo using acoustic radiation force," Ultrasound in Medicine and Biology, vol. 34, pp. 546-558, Apr. 2008.
Palmeri, M. L., et al. "A finite-element method model of soft tissue response to impulsive acoustic radiation force." EEE transactions on ultrasonics, ferroelectrics, and frequency control 52.10 (2005): 1699-1712.
Pinton, G. F. et al, "Rapid tracking of small displacements with ultrasound," IEEE Transactions on Ultrasonics Ferroelectrics and Frequency Control, vol. 53, pp. 1103-1117, Jun. 2006.
Pinton, G. F. et al, "Sources of image degradation in fundamental and harmonic ultrasound imaging using nonlinear, full-wave simulations," Ultrasonics, Ferroelectrics, and Frequency Control, IEEE Transactions on, vol. 58, pp. 754-765, 2011.
Popescu, A. et al, "The Influence of Food Intake on Liver Stiffness Values Assessed by Acoustic Radiation Force Impulse Elastography—Preliminary Results," Ultrasound in Medicine & Biology, vol. 39, pp. 579-584, 2013.
Radiological Society of North America. (2012). Quantitative Imaging Biomarker Alliance (RSNA QIBA) Ultrasound Shear Wave Speed Technical Committee. Available: http://qibawiki.rsna.org/index.php?title=Ultrasound_SWS_tech_ctte. Version as of Dec. 11, 2012. Accessed Dec. 17, 2019.
Rouze, N.C. et al., "Robust Estimation of Time-of-Flight Shear Wave Speed Using a Radon Sum Transformation," IEEE transactions on ultrasonics, ferroelectrics, and frequency control, vol. 57, pp. 2662-2670, 2010.
Sandrin, L. et al, "Shear modulus imaging with 2-D transient elastography," IEEE Transactions on Ultrasonics Ferroelectrics and Frequency Control, vol. 49, pp. 426-435, Apr. 2002.

(56) References Cited

OTHER PUBLICATIONS

Sarvazyan, A.P. et al, "Shear wave elasticity imaging: A new ultrasonic technology of medical diagnostics," Ultrasound Med. Biol., vol. 24, pp. 1419-1435, 1998.

Song, P. et al., "Comb-push Ultrasound Shear Elastography (CUSE): A Novel Method for Two-dimensional Shear Elasticity Imaging of Soft Tissues," Ieee Transactions on Medical Imaging, vol. 31, pp. 1821-1832, 2012.

Song, P. et al, "Fast shear compounding using directional filtering and two-dimensional shear wave speed calculation." 2013 IEEE International Ultrasonics Symposium (IUS). IEEE, 2013.

Song, P. et al, "Fast Shear Compounding Using Robust 2-D Shear Wave Speed Calculation and Multi-directional Filtering," Ultrasound in Medicine & Biology, vol. 40, pp. 1343-1355, 2014.

Song, P. et al, "Two-dimensional shear-wave elastography on conventional ultrasound scanners with time-aligned sequential tracking (TAST) and comb-push ultrasound shear elastography (CUSE)," IEEE transactions on ultrasonics, ferroelectrics, and frequency control, vol. 62, pp. 290-302, 2015.

Tanter, M. et al, "Quantitative Assessment of Breast Lesion Viscoelasticity: Initial Clinical Results Using Supersonic Shear Imaging," Ultrasound in Medicine & Biology, vol. 34, pp. 1373-1386, 2008.

Urban M.W. et al, "Use of the radon transform for estimation of shear wave speed," The Journal of the Acoustical Society of America, vol. 132, pp. 1982-1982, 2012.

Venkatesh, S. K. et al., "Magnetic Resonance Elastography of Liver: Technique, Analysis and Clinical Applications," Journal of magnetic resonance imaging : JMRI, vol. 37, pp. 544-555, 2013.

Wang, M. et al, "On the precision of time-of-flight shear wave speed estimation in homogeneous soft solids: initial results using a matrix array transducer," IEEE transactions on ultrasonics, ferroelectrics, and frequency control, vol. 60, pp. 758-770, 2013.

Wang, M. H., et al. "Improving the robustness of time-of-flight based shear wave speed reconstruction methods using RANSAC in human liver in vivo." Ultrasound in medicine & biology 36.5 (2010): 802-813.

Xie, H. et al, "Shear wave Dispersion Ultrasound Vibrometry (SDUV) on an ultrasound system: In vivo measurement of liver viscoelasticity in healthy animals," in Ultrasonics Symposium (IUS), 2010 IEEE, 2010, pp. 912-915.

Yin, M. et al, "Assessment of Hepatic Fibrosis With Magnetic Resonance Elastography," Clinical Gastroenterology and Hepatology, vol. 5, pp. 1207-1213.e2, 2007.

International Search Report and Written Opinion from PCT/US2017/022221, dated May 25, 2017, 18 pages.

\* cited by examiner

SHEAR WAVE GROUP VELOCITY ESTIMATION USING SPATIOTEMPORAL PEAKS AND AMPLITUDE THRESHOLDING

CROSS-REFERENCE TO RELATED APPLICATIONS

This application is a 371 U.S. National Phase entry of International Application No.: PCT/US2017/022221, filed Mar. 17, 2017, which claims the benefit of U.S. Provisional Patent Application Ser. No. 62/307,764, filed on Mar. 14, 2016, and entitled "SHEAR WAVE GROUP VELOCITY ESTIMATION USING SPATIOTEMPORAL PEAKS AND AMPLITUDE THRESHOLDING."

STATEMENT REGARDING FEDERALLY SPONSORED RESEARCH

This invention was made with government support under DK092255 awarded by the National Institutes of Health. The government has certain rights in the invention.

BACKGROUND

The field of the present disclosure is systems and methods for shear wave elastography. More particularly, the present disclosure relates to systems and methods for estimating shear wave group velocity from shear wave elastography data.

Soft tissue elasticity is associated with tissue health. Noninvasive quantification of soft tissue elasticity can therefore be used for noninvasive assessment of tissue health, such as by assessing chronic disease such as liver fibrosis. Examples of elasticity imaging techniques include magnetic resonance elastography ("MRE"), transient elastography ("TE"), quasi-static elastography, acoustic radiation force impulse imaging ("ARFI"), shear wave elasticity imaging ("SWEI"), and supersonic shear wave imaging ("SSI").

SWEI methods generate shear waves inside a tissue-of-interest, and the shear wave propagation is then monitored in space and time by a real-time imaging modality. Soft tissue stiffness is then estimated from the measured shear wave propagation velocity. There are several methods to estimate the shear wave velocity from the shear wave propagation data, including the algebraic inversion method, the local frequency estimation ("LFE") method, correlation-based methods, Radon transform methods, and the time-to-peak ("TTP") method.

Although LFE does not require second order derivative calculations, as in algebraic inversion methods, both methods are limited in ultrasound elastography applications because of the noisy nature in ultrasound motion signals. Correlation-based methods find the shear wave arrival time by cross-correlating the displacement time history of a spatial point against the displacement time history at a nearby reference point. The shear wave arrival time is then used in a time-of-flight algorithm to resolve the shear wave group velocity. Cross-correlation based methods are used to create group velocity maps, as in SSI, spatially-modulated ultrasound radiation force ("SMURF"), and comb-push ultrasound shear elastography ("CUSE"). The Radon transform method uses the Radon transform or a Radon sum on the spatiotemporal shear wave data to estimate the shear wave group velocity.

The TTP method assumes a pure elastic medium and a fixed propagation direction. The shear wave arrival time is then estimated at each spatial location and the shear wave velocity is calculated by a linear regression of those arrival times versus distance. The TTP method has been used with ultrasound SWEI methods; however, in vivo motion characteristics (e.g., low signal-to-noise ratio, physiological motion, tissue inhomogeneity, viscoelasticity) can affect the shear wave speed estimation.

Different techniques have been suggested to improve the outcome of the TTP algorithm for in vivo applications, including averaging shear wave speed estimation over locations within an image or implementing repeated measurements and using the goodness of linear fit to remove failed measurements.

Recently, an iterative linear fitting method called random sample consensus ("RANSAC") was suggested to improve the robustness of the TTP method. Although the RANSAC implementation improves the shear wave group velocity estimation for the TTP method, the RANSAC algorithm is working in the presence of minority outliers while doing a linear fit to the majority inliners.

There is still a need for methods that can improve shear wave propagation detection in the presence of very noisy motion data, where outliers are no longer the minority.

SUMMARY OF THE DISCLOSURE

The present disclosure addresses the aforementioned drawbacks by providing a computer-implemented method for estimating a shear wave velocity from elastography data acquired with an elastography system. Elastography data are provided to a computer system, from which a motion profile is generated for each of a plurality of spatial locations in a field-of-view. Each motion profile represents motion over a plurality of time points. Temporal peak data are then generated by determining for each spatial location, a time point at which motion at the spatial location is at a maximum. Similarly, spatial peak data are generated by determining for each time point, a spatial location at which motion at the time point is at a maximum. The shear wave velocity is then estimated based on a fitting of the temporal peak data and the spatial peak data, and an output that indicates the estimated shear wave velocity is generated.

It is an aspect of the present disclosure to provide a computer-implemented method for estimating a shear wave velocity from elastography data acquired with an elastography system. Elastography data are provided to a computer system, from which a motion profile is generated for each of a plurality of spatial locations in a field-of-view. Each displacement profile represents motion over a plurality of time points. Temporal peak data are then generated by determining for each spatial location, a time point at which motion at the spatial location is at a maximum. Similarly, spatial peak data are generated by determining for each time point, a spatial location at which motion at the time point is at a maximum. Temporally normalized motion profiles are then generated by normalizing the motion profiles using the temporal peak data, and spatially normalized motion profiles are generated by normalizing the motion profiles using the spatial peak data. Thresholded temporal data are then generated by thresholding the temporally normalized motion profiles using a motion amplitude threshold value, and thresholded spatial data are generated by thresholding the spatially normalized motion profiles using the motion amplitude threshold value. The shear wave velocity is then estimated based on a fitting of the thresholded temporal data and the thresholded spatial data, and an output that indicates the estimated shear wave velocity is generated.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for estimating shear wave velocity from data acquired with a shear wave elastography system. More particularly, the systems and methods described here implement a spatiotemporal time-to-peak algorithm that searches for the times at which shear wave motion is at a maximum while also searching for the lateral locations at which shear wave motion is at a maximum. Here, motion can include displacement, velocity, or acceleration. A fitting procedure (e.g., a linear fit) is performed on a combined set of these temporal peaks and spatial peaks to estimate the shear wave velocity, from which mechanical properties can be computed. Conventional time-to-peak algorithms are limited to searching for the maximum shear wave displacement in time profiles at different spatial locations.

In some embodiments, the temporal and spatial peak data are thresholded to improve the shear wave velocity estimation, as will be described in more detail below. For example, an amplitude filter can be utilized to increase the number of points that are used to estimate the group velocity.

Figure 1:
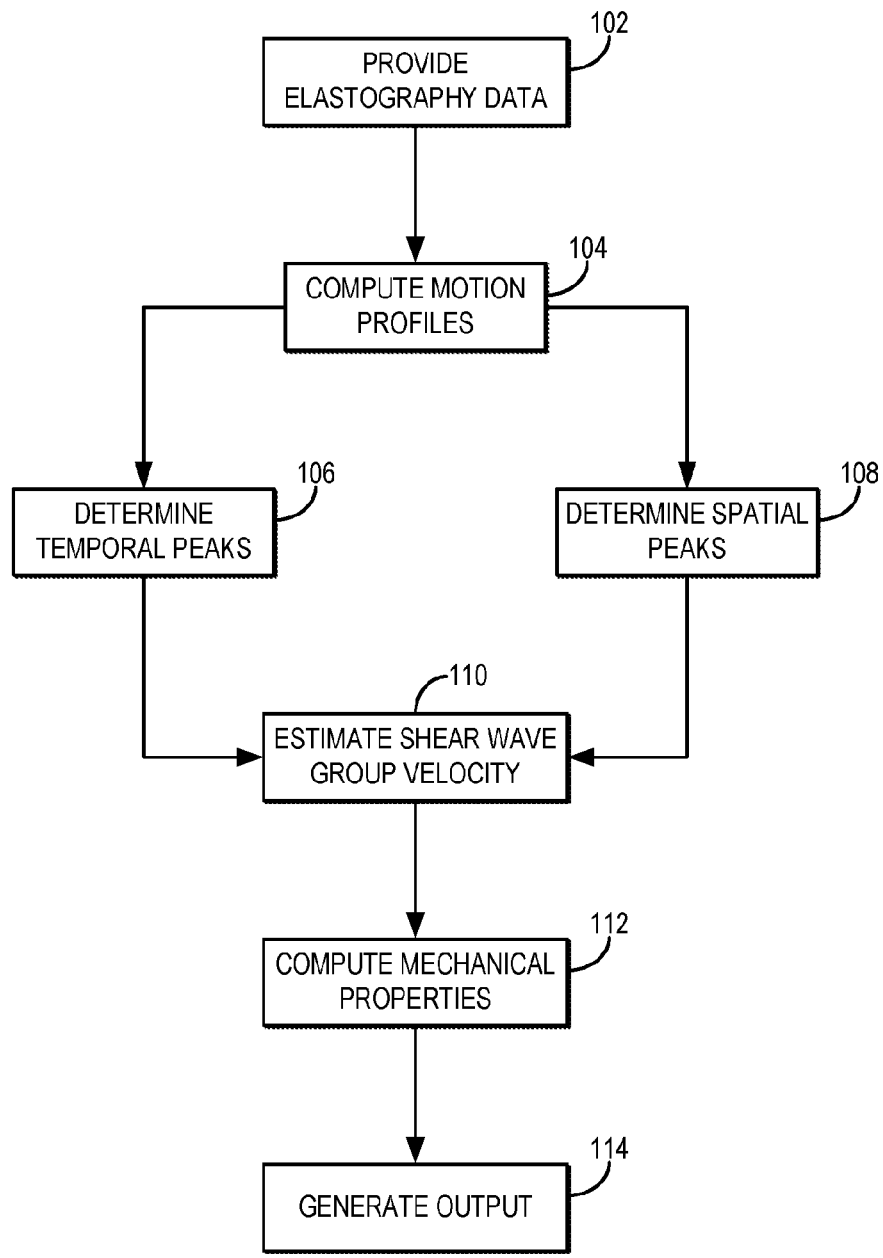
FIG. 1 is a flowchart setting forth the steps of an example method for estimating shear wave velocity using a spatiotemporal time-to-peak method.

Referring now to FIG. 1, a flowchart is illustrated as setting forth the steps of an example method for estimating shear wave velocity using a spatiotemporal time-to-peak algorithm. The method includes providing elastography data to a computer system, as indicated at step 102. In general, elastography data include measurements of shear waves propagating through an object or subject imaged with a shear wave elastography system. This elastography data will be processed to estimate the shear wave velocity, from which mechanical properties can be estimated. In some embodiments, elastography data can be provided to the computer system by retrieving such data from a data storage. In some other embodiments, elastography data can be provided to the computer system by acquiring such data using a shear wave elastography system. The shear wave elastography system can include an ultrasound shear wave elastography system, a magnetic resonance imaging ("MRI") system operating a magnetic resonance elastography scan, and so on.

As indicated at step 104, the elastography data is processed to compute motion profiles indicating the shear wave motion in the object or subject that was imaged. The motion profiles can include displacement profiles indicating displacement, velocity profiles indicating velocity, or acceleration profiles indicating acceleration. As one example, the motion profiles can be computed using an autocorrelation method. The motion profiles are then processed to determine temporal peaks, as indicated at step 106, and spatial peaks, as indicated at step 108.

Temporal peaks are those time points at which maximum shear wave motion occurred at a given lateral location. For motion profiles, u(x,t), corresponding to $N_x$ different lateral locations each sampled at $N_t$ different time points, the temporal peak at the $i^{th}$ lateral location, $x_i$, can be determined according to, $$TP_i = \arg\max\{u(x_i,t)\} \quad (1).$$

Spatial peaks are those lateral locations at which maximum shear wave motion occurred at a given time point. For motion profiles, u(x,t), corresponding to $N_x$ different lateral locations each sampled at $N_t$ different time points, the spatial peak at the $j^{th}$ time point, $t_j$, can be determined according to, $$LP_j = \arg\max\{u(x,t_j)\} \quad (2),$$

The temporal peaks, $TP_i$, and spatial peaks, $LP_j$, can be combined in a set, $$S = \{[x,TP_i],[LP_j,t]\} \quad (3);$$

which is then processed to estimate the shear wave velocity, as indicated at step 110. In some embodiments, the shear wave velocity can be estimated using a fitting procedure on the set of temporal and spatial peaks. As one example, a random sampling consensus ("RANSAC") iterative linear fitting technique can be implemented to estimate the shear wave velocity based on the temporal and spatial peaks. Different linear fitting techniques can also be implemented, including linear regression with least squares, linear regression with weighted least squares, and RANSAC using a weighting in the cost function. In the instances where weightings are used, those weightings can be based on motion amplitudes.

Using the estimated shear wave velocity, mechanical properties of the object or subject imaged can be computed, as indicated at step 112. Examples of mechanical properties and related measurement that can be computed include, but are not limited to, shear stress, shear strain, Young's modulus, shear modulus, storage modulus, loss modulus, viscosity, and anisotropy.

An output is then generated by the computer system, as indicated at step 114. The output can include storing motion profiles, temporal peak data, spatial peak data, shear wave velocity data, mechanical property data, or other such data, in a data storage. The output can also include displaying motion profiles, temporal peak data, spatial peak data, shear wave velocity data, mechanical property data, or other such data, to a user, such as by displaying the data on an electronic display device. In some instances, data can be displayed as two-dimensional images. Such images could include shear wave velocity maps that depict shear wave velocity at the lateral locations in the object or subject that was imaged, or could include mechanical property images that depict one or more mechanical properties at the lateral locations in the object of subject that was imaged.

Figure 2:
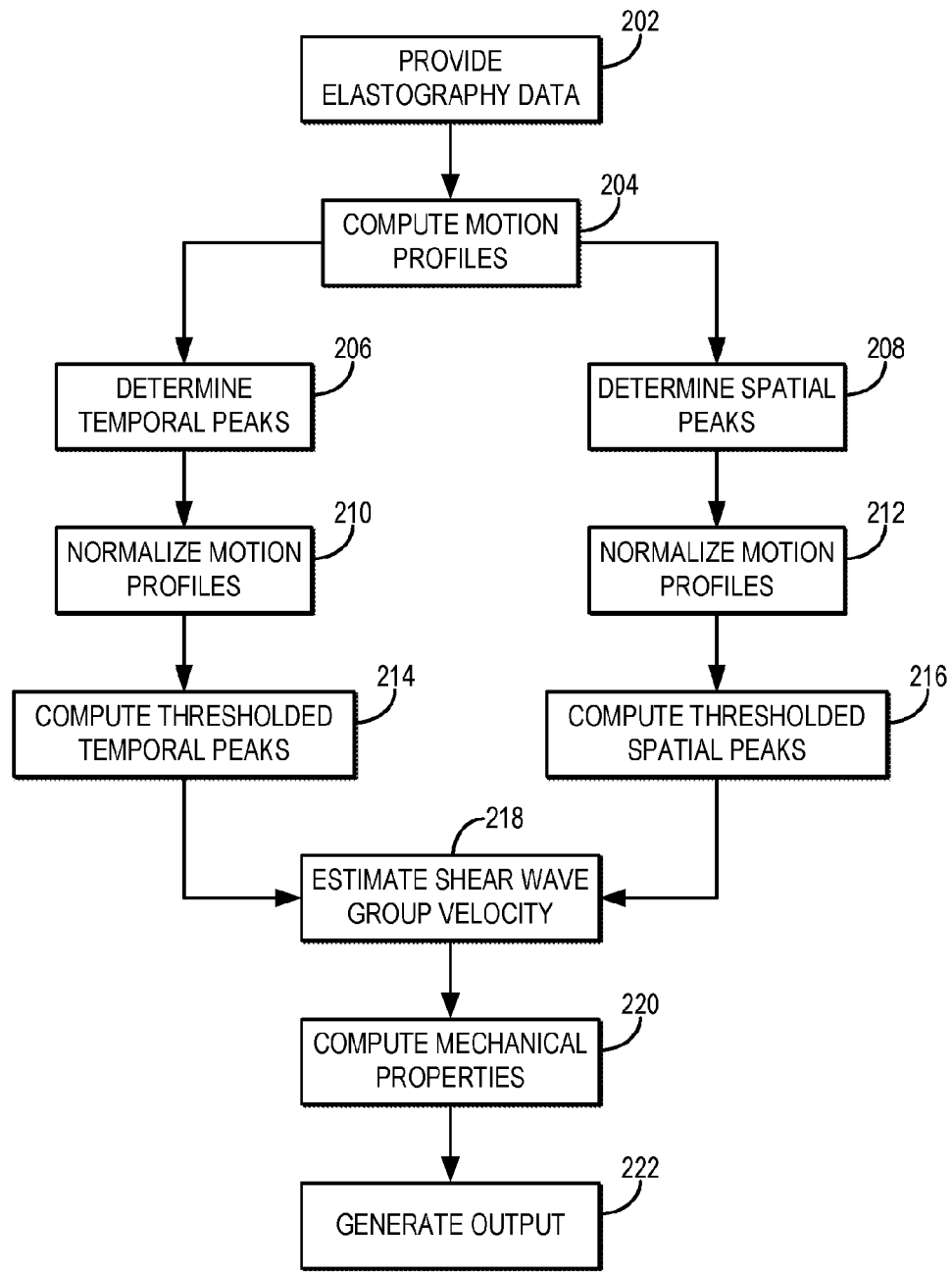
FIG. 2 is a flowchart setting forth the steps of an example method for estimating shear wave velocity using a spatiotemporal time-to-peak with amplitude thresholding method.

Referring now to FIG. 2, a flowchart is illustrated as setting forth the steps of an example method for estimating shear wave velocity using a spatiotemporal time-to-peak algorithm with amplitude thresholding. The method includes providing elastography data to a computer system, as indicated at step 202. As mentioned above, in some embodiments, elastography data can be provided to the computer system by retrieving such data from a data storage. As also mentioned above, in some other embodiments, elastography data can be provided to the computer system by acquiring such data using a shear wave elastography system.

As indicated at step 204, the elastography data is processed to compute motion profiles indicating the shear wave motion in the object or subject that was imaged. The motion profiles can include displacement profiles indicating displacement, velocity profiles indicating velocity, or acceleration profiles indicating acceleration. As one example, the motion profiles can be computed using an autocorrelation method. The motion profiles are then processed to determine temporal peaks, as indicated at step 206, and spatial peaks, as indicated at step 208.

Temporal peaks are those time points at which maximum shear wave motion occurred at a given lateral location. For motion profiles, u(x,t), corresponding to $N_x$ different lateral locations each sampled at $N_t$ different time points, the temporal peak at the $i^{th}$ lateral location, $x_i$, can be determined according to, $$TP_i = \arg\max\{u(x_i,t)\} \quad (4).$$

Spatial peaks are those lateral locations at which maximum shear wave motion occurred at a given time point. For motion profiles, u(x,t), corresponding to $N_x$ different lateral locations each sampled at $N_t$ different time points, the spatial peak at the $j^{th}$ time point, $t_j$, can be determined according to, $$LP_j = \arg\max\{u(x,t_j)\} \quad (5).$$

Using the temporal peaks, $TP_i$, temporally normalized motion profiles are generated, as indicated at step 210. Similarly, using the spatial peaks, $LP_j$, spatially normalized motion profiles are generated, as indicated at step 212. The temporally normalized motion profiles, $u_N(x_i, t)$, can be generated according to, $$u_N(x_i, t) = \frac{u(x_i, t)}{TP_i}; \quad (6)$$

and the spatially normalized motion profiles, $u_N(x, t_j)$, can be generated according to, $$u_N(x, t_j) = \frac{u(x, t_j)}{LP_j}. \quad (7)$$

Thresholded temporal peak data are then generated by thresholding the temporally normalized motion profiles, as indicated at step 214. These thresholded temporal peak data, $TP_{i,T}$, can be generated according to, $$TP_{i,T} = u_N(x_i,t) \geq T \quad (8);$$

where T is an amplitude threshold value. As an example, the amplitude threshold value can be a percentage (e.g., 80 percent) of the local maximum shear wave motion (e.g., displacement, velocity, acceleration). Similarly, thresholded spatial peak data are generated by thresholding the spatially normalized motion profiles, as indicated at step 216. These thresholded spatial peak data, $LP_{j,T}$, can be generated according to, $$LP_{j,T} = u_N(x,t_j) \geq T \quad (9).$$

In some instances, the same amplitude threshold value, T, is used to generate both the thresholded temporal peak data and the thresholded spatial peak data; however, in some instances a different amplitude threshold value can be used for generating the thresholded temporal peak data than is used to generate the thresholded spatial peak data.

The thresholded temporal and spatial peak data can be combined in a set, $$S_T = \{[x, TP_{i,T}], [LP_{j,T}, t]\} \quad (10);$$

which is then processed to estimate the shear wave velocity, as indicated at step 218. In some embodiments, the shear wave velocity can be estimated using a fitting procedure on the set of thresholded temporal and spatial peaks. As one example, a random sampling consensus ("RANSAC") iterative linear fitting technique can be implemented to estimate the shear wave velocity based on the thresholded temporal and spatial peaks.

Using the estimated shear wave velocity, mechanical properties of the object or subject imaged can be computed, as indicated at step 220. Examples of mechanical properties and related measurements that can be computed include, but are not limited to, shear stress, shear strain, Young's modulus, shear modulus, storage modulus, loss modulus, viscosity, and anisotropy.

An output is then generated by the computer system, as indicated at step 222. The output can include storing motion profiles, temporally normalized motion profiles, spatially normalized motion profiles, temporal peak data, thresholded temporal peak data, spatial peak data, thresholded spatial peak data, shear wave velocity data, mechanical property data, or other such data, in a data storage. The output can also include displaying motion profiles, temporally normalized motion profiles, spatially normalized motion profiles, temporal peak data, thresholded temporal peak data, spatial peak data, thresholded spatial peak data, shear wave velocity data, mechanical property data, or other such data, to a user, such as by displaying the data on an electronic display device. In some instances, data can be displayed as two-dimensional images. Such images could include shear wave velocity maps that depict shear wave velocity at the lateral locations in the object or subject that was imaged, or could include mechanical property images that depict one or more mechanical properties at the lateral locations in the object of subject that was imaged.

Figures 3A, 3B, 3C, 3D, 3E:
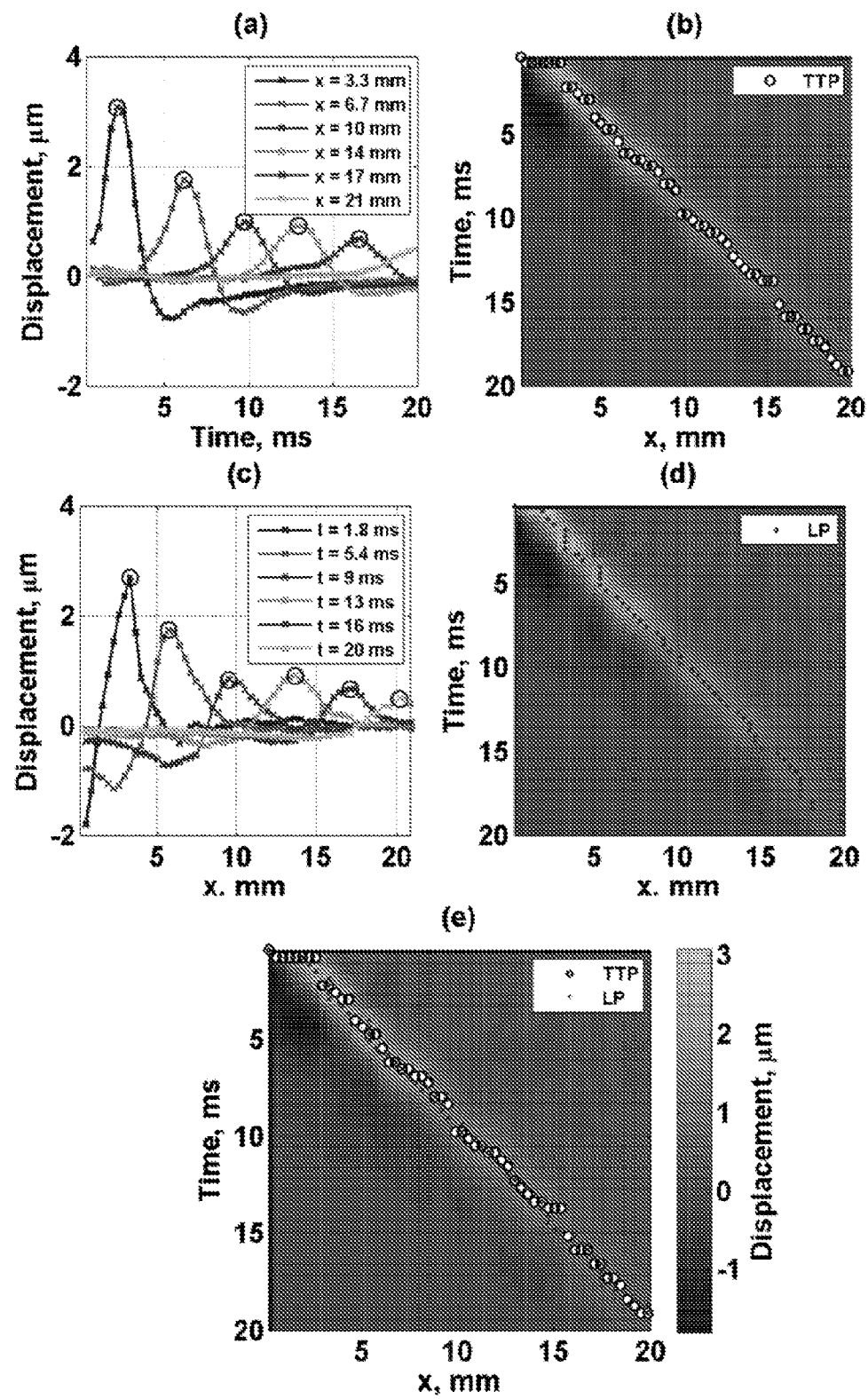
FIG. 3A-3E show experimental data acquired from a phantom and illustrating the spatiotemporal time-to-peak method of FIG. 1.

FIGS. 3A-3E illustrate experimental data acquired from a tissue mimicking phantom and processed according to the spatiotemporal time-to-peak method described above. FIG. 3A shows shear wave displacement as a function of lateral location (the circles represent the time-to-peak (TTP)). FIG. 3B shows a spatiotemporal shear wave displacement map with TTP locations (black and white circles). FIG. 3C shows shear wave spatial profiles at different time instances (the circles represent the lateral location peak (LP)). FIG. 3D shows a spatiotemporal shear wave displacement map with LP locations (red closed circles). FIG. 3E shows a spatiotemporal shear wave displacement map with combination of TTP (black and white circles) and LP (red closed circles) locations.

Figure 4A:
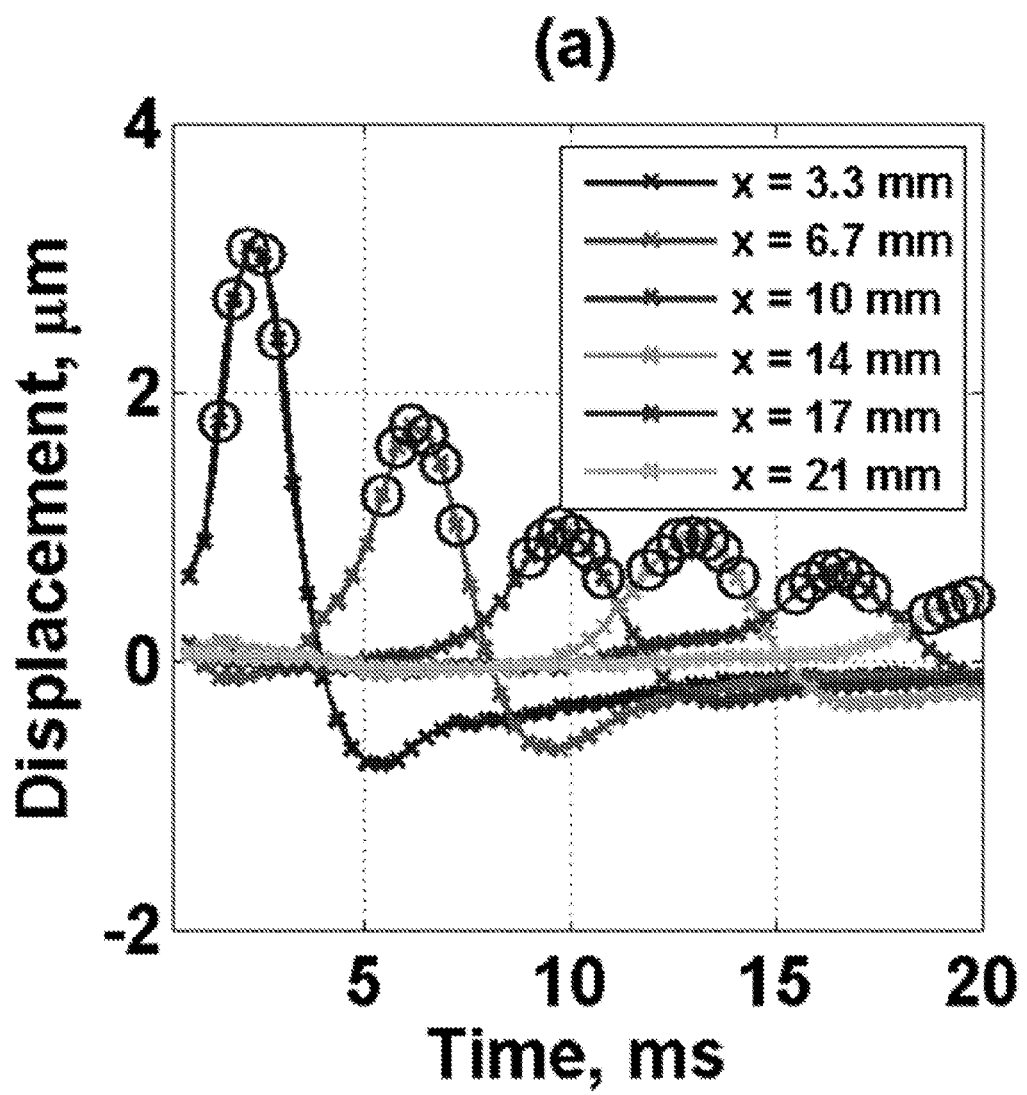
FIG. 4A-4E show experimental data acquired from a phantom and illustrating the spatiotemporal time-to-peak with amplitude thresholding method of FIG. 2.
Figure 4B:
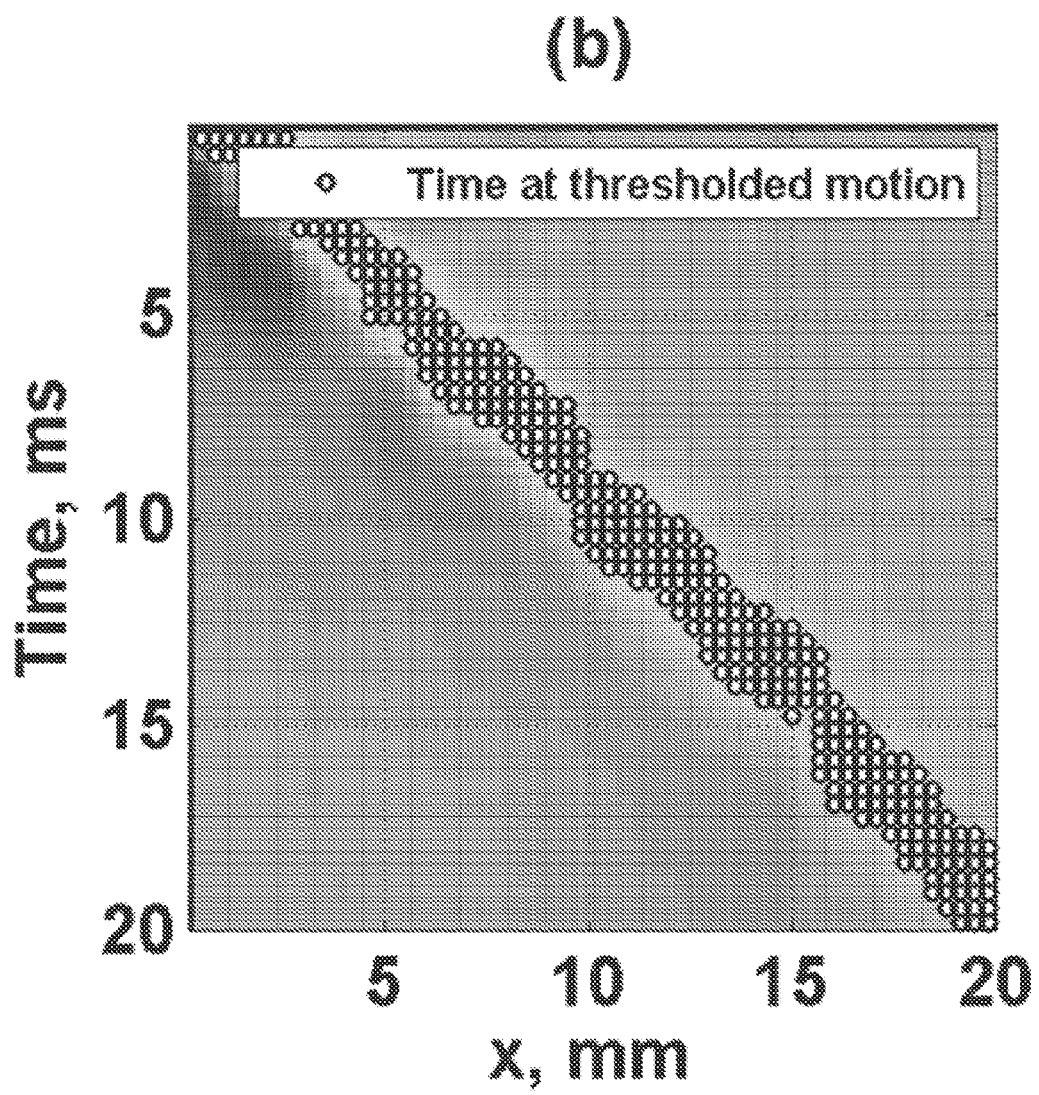
Figure 4C:
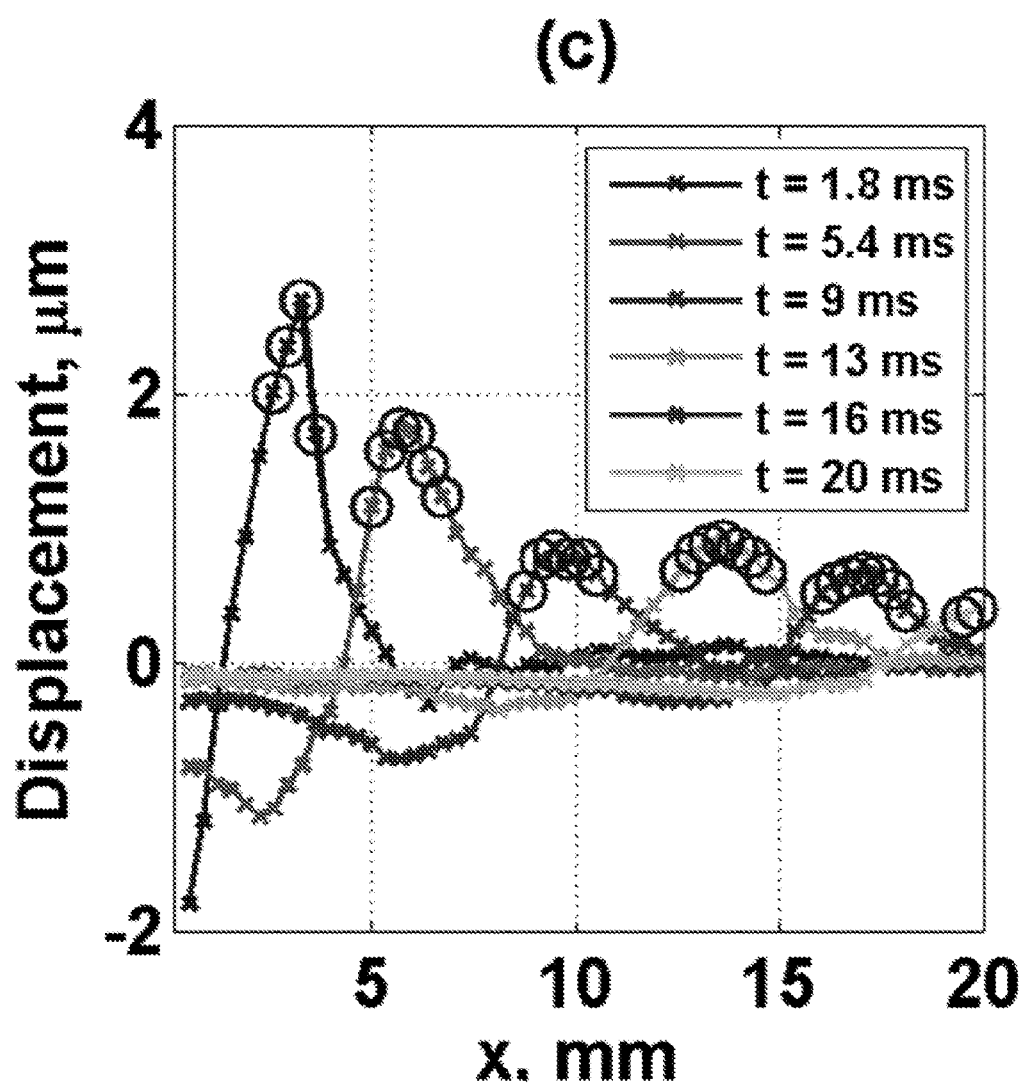
Figure 4D:
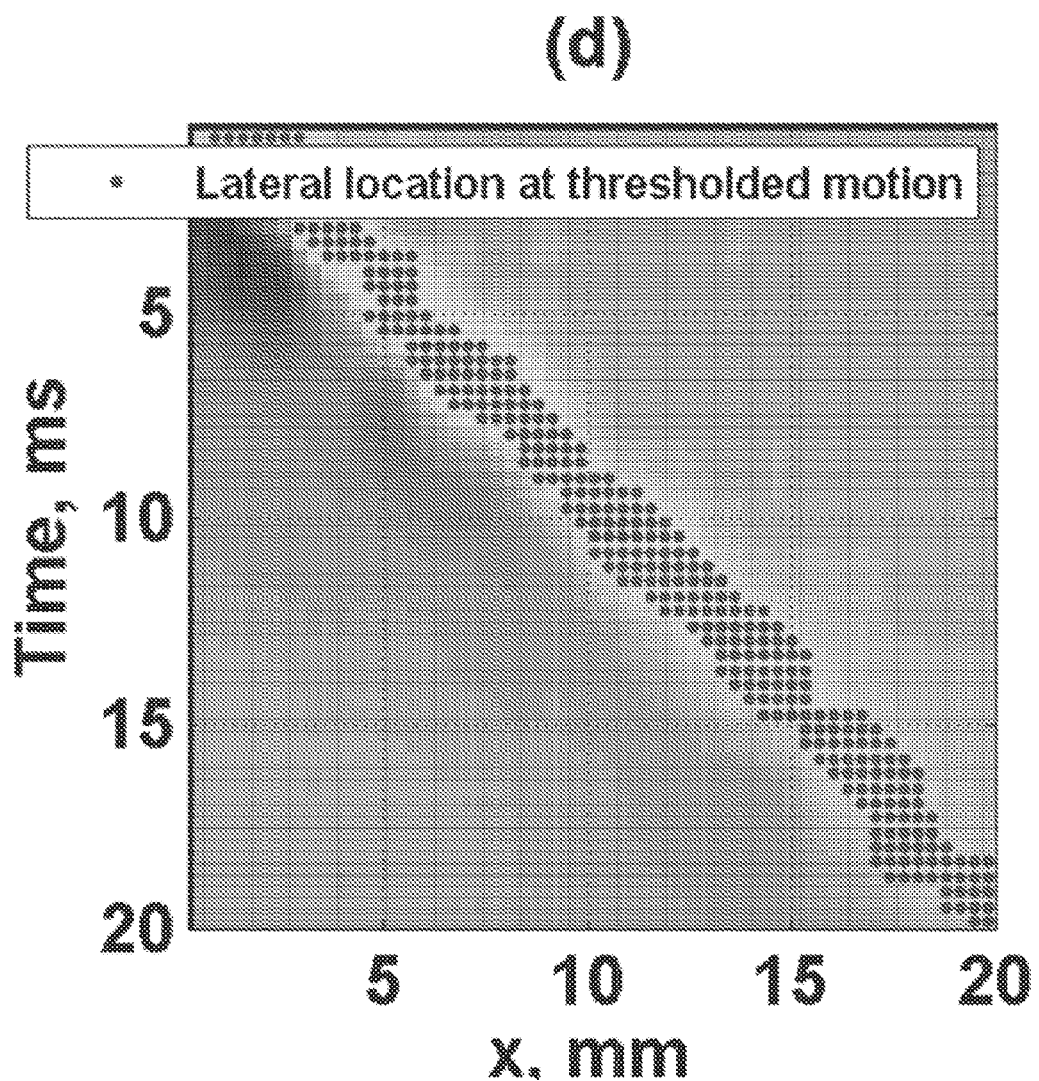
Figure 4E:
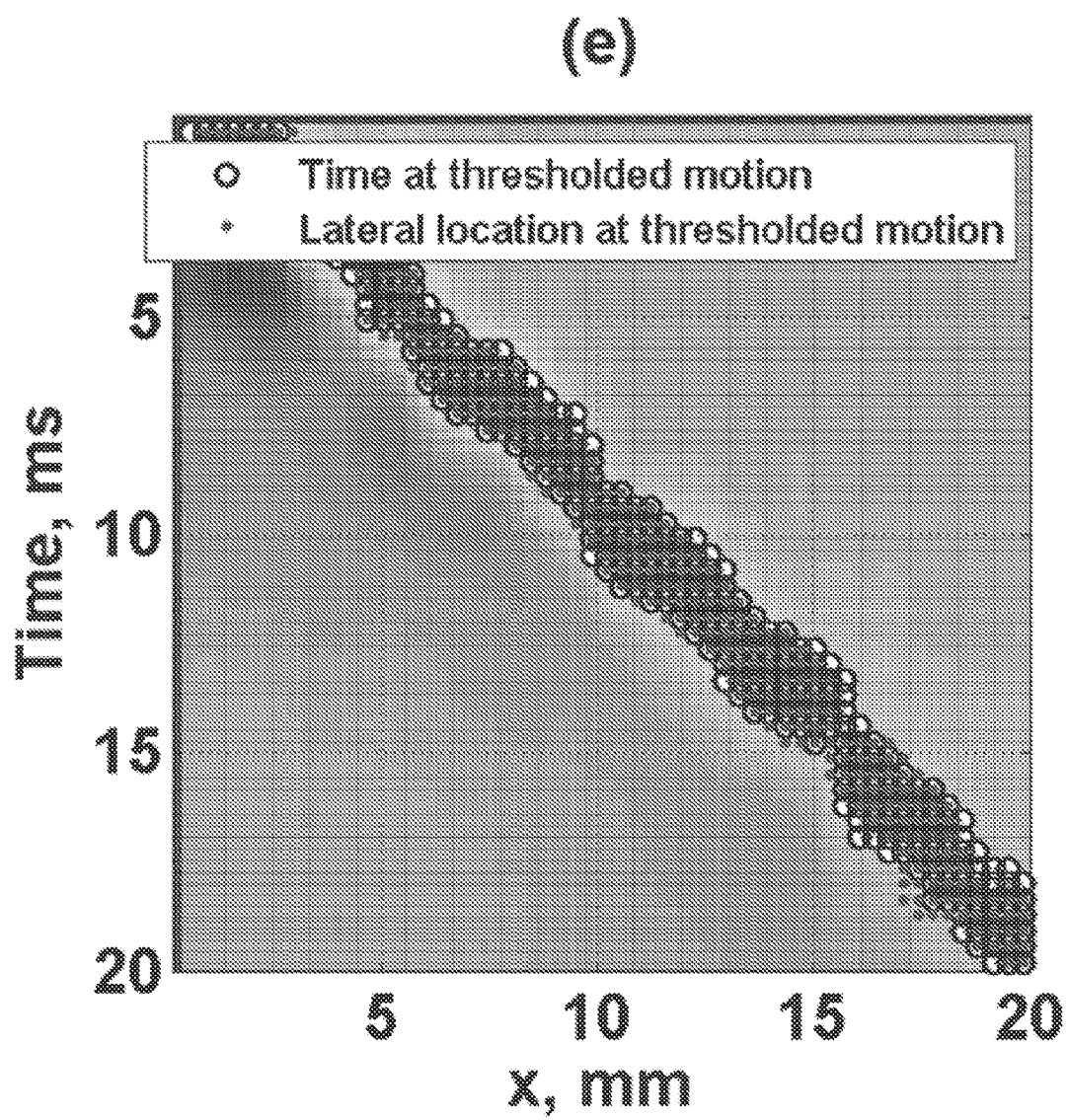

FIGS. 4A-4E illustrate experimental data acquired from a tissue mimicking phantom. FIG. 4A shows shear wave displacement as a function of lateral location (the circles represent the time at which the motion is more than 0.80 times the local maximum). FIG. 4B shows a spatiotemporal shear wave displacement map with time points at which the local motion is more than 0.80 times the local maximum (black and white circles). FIG. 4C shows shear wave displacement as a function of time (the circles represent the lateral location at which the motion is more than 0.80 times the local maximum). FIG. 4D shows a spatiotemporal shear wave displacement map with lateral points at which the local motion is more than 0.80 times the local maximum (red closed circles). FIG. 4E shows a spatiotemporal shear wave displacement map with combination of time (black and white circles) and lateral (red closed circles) points at which the motion is more than 0.80 times the local maximum.

The spatiotemporal time-to-peak and the spatiotemporal time-to-peak algorithm with amplitude thresholding methods described above were described in one-dimension; however, they can be extended to two-dimensional ("2D") and three-dimensional ("3D") reconstructions to create 2D and 3D images of the group velocity.

Figure 5A:
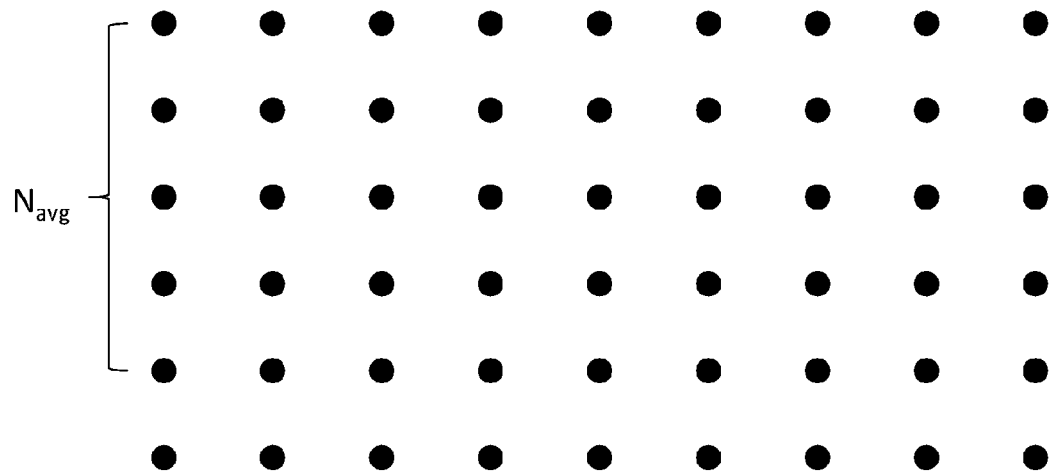
FIG. 5A depicts the averaging of several lines of motion data with $N_{avg}$ lines.
Figure 5B:
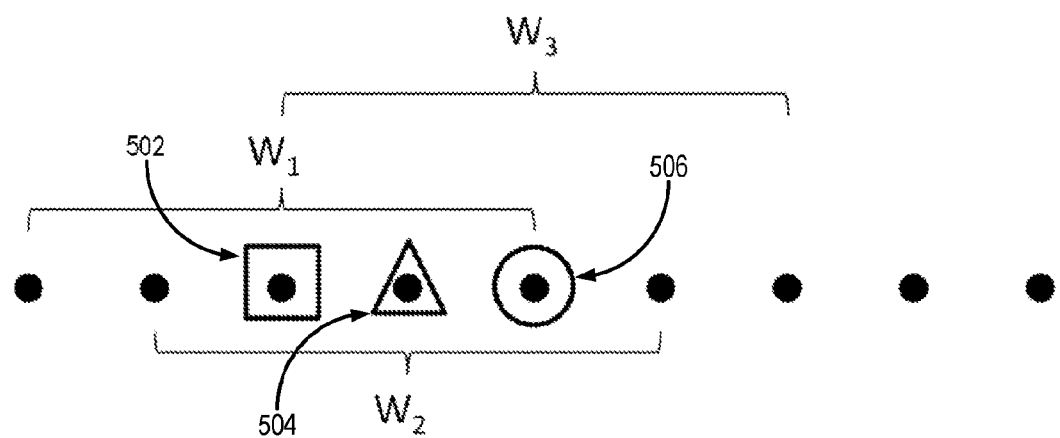
FIG. 5B depicts applying sliding windows, $W_i$, with $N_x$ points and $N_{overlap}$ overlapping points to data, and applying spatiotemporal time-to-peak or spatiotemporal time-to-peak with amplitude thresholding algorithms based on the sliding windows.

As one example, a sliding window can be applied in those instances where the waves are predominantly traveling in the x-direction, whether positive or negative. The data can be averaged over one to $N_{avg}$ lines in depth (i.e., the z-direction). The window is defined as having $N_x$ spatial points. The spatiotemporal time-to-peak algorithm, or spatiotemporal time-to-peak algorithm with amplitude thresholding method, can be applied to the averaged data over the $N_x$ spatial points, and the group velocity value found can be inserted at the point in the middle of the $N_x$ window, such as round($N_x/2$). The window can be moved to be centered about each pixel in the image. The window can also be adaptively changed in size near the border, which can reduce truncation of the resulting image to accommodate the $N_x$ window. The sliding window process can have a number of pixels with overlap, $N_{overlap}$. In the example shown in FIG. 5A, the data is averaged over five lines (i.e., $N_{avg}=5$). In FIG. 5B, $N_x=5$ and $N_{overlap}=4$.

In FIG. 5B, the square 502 is the result of applying the spatiotemporal time-to-peak algorithm or spatiotemporal time-to-peak algorithm with amplitude thresholding method over the window $W_1$. Likewise, the triangle 504 and the circle 506 are the results of applying one of the algorithms over the windows $W_2$ and $W_3$, respectively. The averaging window in the z-direction would then be moved and the process would be repeated for another line to build up the 2D group velocity map.

The quality of the measurements for any window can be evaluated by the inlier ratio or another quality metric, such as the motion amplitude or a parameter related to the RANSAC fit such as the coefficient of determination, $R^2$.

A 2D group velocity method that takes into account a wave traveling at an arbitrary angle can also be used, similar to the methods described by P. Song, et al., in "Fast shear compounding using robust 2-D shear wave speed calculation and multi-directional filtering," *Ultrasound Med. Biol.*, 2014; 40:1343-1355. The 1D sliding window method described above can be applied in the x-direction to obtain the velocity in the x-direction, $V_x$. A 1D window with $N_z$ points can be used in the z-direction similar to the way the $N_x$ length window is used in the x-direction to obtain an estimate of the velocity in the z-direction, $V_z$. The resultant velocity, V, can then be found using the following equation:

$$V = \frac{V_x V_z}{\sqrt{V_x^2 + V_z^2}}. \quad (11)$$

An Andersson-Hegland approach could also be used to use a window, W×W, and small patches of length, p, as also described by P. Song, et al., in "Fast shear compounding using robust 2-D shear wave speed calculation and multi-directional filtering," *Ultrasound Med. Biol.*, 2014; 40:1343-1355. The spatiotemporal time-to-peak algorithms or spatiotemporal time-to-peak algorithm with amplitude thresholding algorithms described in the present disclosure can be applied to each patch to obtain an estimate of $V_x$ and $V_z$. The values of $V_x$ and $V_z$ can then be weighted by the $R^2$ value or inlier ratio along with the inverse distance to derive a resulting estimate of $V_x$ and $V_z$ for the window centered at a pixel (m, n). This window function can be raster-scanned over the 2D field to construct an image.

An additional approach is to use a 2D formulation of the RANSAC algorithm, such as the one described by M. H. Wang, et al., in "Improving the robustness of time-of-flight based shear wave speed reconstruction methods using RANSAC in human liver in vivo," *Ultrasound Med. Biol.*, 2010; 36:802-813. A window of $N_x \times N_z$ pixels can be extracted and fit using the spatiotemporal time-to-peak algorithm or spatiotemporal time-to-peak algorithm with amplitude thresholding approaches with a 2D RANSAC implementation as opposed to the 1D version of the RANSAC algorithm previously described. The result of the wave velocity calculation would be placed at the center pixel of the $N_x \times N_z$ window. The $N_x \times N_z$ window can be raster scanned over the 2D plane to form a 2D image of the group velocity.

An additional step that can be involved is the use of a directional filter applied to the motion data to extract $N_{DF}$ motion fields to account for shear waves propagating at different angles within the field of view. The sliding window algorithm described above can then be used on each of the resulting $N_{DF}$ motion fields. The results can then be averaged together and weighted by the inlier ratio or another quality metric such as the motion amplitude or a parameter related to the RANSAC fit. This weighted average will yield a final group velocity image.

Each of these approaches described above could also be extended to 3D data to produce 3D maps of group velocity by similar modifications to include the y-direction.

Figure 6:
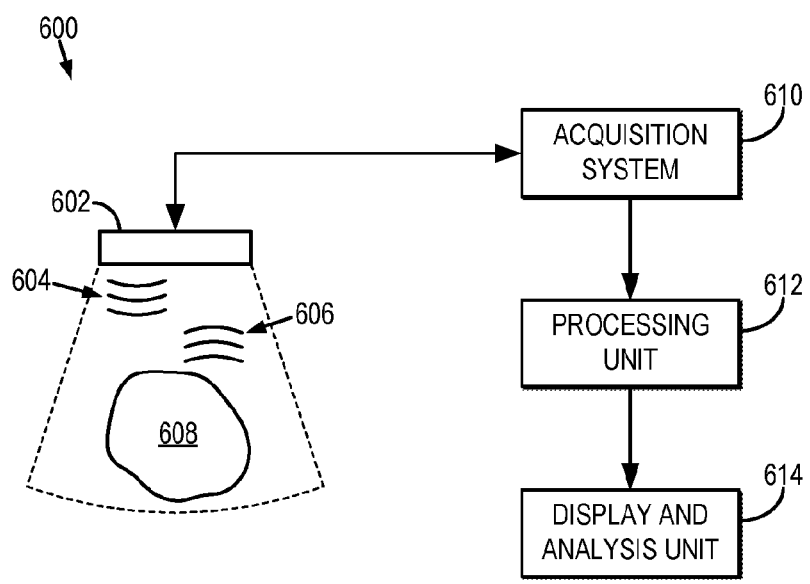
FIG. 6 is a block diagram of an example ultrasound elastography imaging system that can implement the methods described here.

FIG. 6 illustrates the main components of an example ultrasound imaging system 600 that can be operated to perform shear wave elastography imaging. The system 600 generally includes an ultrasound transducer 602 that transmits ultrasonic waves 604 and receives ultrasonic echoes 606 from an object 608, which may be tissue in a subject. An acquisition system 610 acquires ultrasound signals from the transducer 602 and outputs the signals to a processing unit 612, which can include a suitable computer system or processor. In some implementations, the acquisition system 610 beamforms the signal from each transducer element channel and outputs the signal to the processing unit 612. The processing unit 612 can be programmed to implement the methods described here for estimating shear wave velocity and computing mechanical properties. The output from the processing unit 612 can be displayed and analyzed by a display and analysis unit 614, which can include a suitable computer display or computer system.

The present disclosure has described one or more preferred embodiments, and it should be appreciated that many equivalents, alternatives, variations, and modifications, aside from those expressly stated, are possible and within the scope of the invention.

The invention claimed is:

1. A computer-implemented method for estimating a shear wave velocity from elastography data acquired with an elastography system, the steps of the method comprising:
   (a) providing the elastography data to a computer system;
   (b) generating from the elastography data, a motion profile for each of a plurality of spatial locations in a field-of-view, each motion profile representing motion over a plurality of time points;
   (c) generating temporal peak data by determining for each spatial location a time point at which motion at the spatial location is at a maximum;
   (d) generating spatial peak data by determining for each time point a spatial location at which motion at the time point is at a maximum;
   (e) estimating the shear wave velocity based on a fitting of the temporal peak data and the spatial peak data; and
   (f) generating an output that indicates the estimated shear wave velocity.

2. The method as recited in claim 1, wherein step (e) includes fitting the temporal peak data and the spatial peak data using a linear fitting.

3. The method as recited in claim 2, wherein the linear fitting is at least one of random sample consensus (RANSAC) linear fitting, weighted RANSAC linear fitting, least squares linear fitting, or weighted least squares linear fitting.

4. The method as recited in claim 3, wherein the RANSAC linear fitting is a two-dimensional RANSAC linear fitting, and the output generated in step (f) is a two-dimensional image of shear wave velocity.

5. The method as recited in claim 1, wherein step (f) includes computing a mechanical property based on the estimated shear wave velocity and generating the output includes generating an output that indicates the mechanical property.

6. The method as recited in claim 1, wherein the motion profiles include at least one of displacement profiles representing displacement over the plurality of time points, velocity profiles representing velocity over the plurality of time points, or acceleration profiles representing acceleration over the plurality of time points.

7. The method as recited in claim 1, wherein:
   step (b) includes spatially averaging multiple motion profiles along a depth direction;
   steps (c)-(e) are repeatedly performed using a sliding window that is moved over data points in the motion profiles to estimate shear wave velocity over a two-dimensional area; and
   step (f) includes generating a two-dimensional image of shear wave velocity in the two-dimensional area.

8. The method as recited in claim 7, wherein in each repetition the sliding window is centered on a different data point and the sliding window is sized to contain a number of overlapping data points in adjacent applications of the sliding window.

9. The method as recited in claim 7, wherein the sliding window is applied along an x-direction.

10. The method as recited in claim 9, further comprising repeating steps (c)(e) with a second sliding window that is applied along the depth direction, and wherein step (f) includes generating the two-dimensional image of shear wave velocity as, $$V = \frac{V_x V_z}{\sqrt{V_x^2 + V_z^2}}$$

wherein $V_x$ is the shear wave velocity estimated along the x-direction and $V_z$ is the shear wave velocity estimated along the depth-direction.

11. The method as recited in claim 9, further comprising repeating steps (c)-(e) with a second sliding window that is moved over data points in the motion profiles along a y-direction to estimate shear wave velocity over a three-dimensional area, and wherein step (f) includes generating a three-dimensional image of shear wave velocity.

12. The method as recited in claim 1, wherein steps (c)-(e) are repeatedly performed along small patches of length p, in a spatial window centered on a pixel to obtain estimates of shear wave velocity along a lateral direction and a depth direction at the pixel, and wherein in each repetition the spatial window is moved to another pixel in a two-dimensional area.

13. The method as recited in claim 12, wherein the estimates of shear wave velocity along the lateral direction and along the depth direction are each weighted by a quality metric.

14. The method as recited in claim 13, wherein the quality metric is one of a motion amplitude, a coefficient of determination, or an inlier ratio.

15. The method as recited in claim 1, wherein:
   step (b) includes directionally filtering the motion profiles to produce multiple motion fields;
   steps (c)-(e) are repeatedly performed using a sliding window that is moved over data points in each of the motion fields to estimate shear wave velocity over a two-dimensional area; and
   step (f) includes generating a two-dimensional image of shear wave velocity in the two-dimensional area.

16. The method as recited in claim 15, wherein the estimates of shear wave velocity are averaged together and weighted by a quality metric.

17. The method as recited in claim 16, wherein the quality metric is one of a motion amplitude, a coefficient of determination, or an inlier ratio.

18. A computer-implemented method for estimating a shear wave velocity from elastography data acquired with an elastography system, the steps of the method comprising:
   (a) providing the elastography data to a computer system;
   (b) generating from the elastography data, a motion profile for each of a plurality of spatial locations in a field-of-view, each motion profile representing motion over a plurality of time points;
   (c) generating temporal peak data by determining for each spatial location a time point at which motion at the spatial location is at a maximum;
   (d) generating spatial peak data by determining for each time point a spatial location at which motion at the time point is at a maximum;
   (e) generating temporally normalized motion profiles by normalizing the motion profiles using the temporal peak data;
   (f) generating spatially normalized motion profiles by normalizing the motion profiles using the spatial peak data;

(g) generating thresholded temporal data by thresholding the temporally normalized motion profiles using a motion amplitude threshold value;

(h) generating thresholded spatial data by thresholding the spatially normalized motion profiles using the motion amplitude threshold value;

(i) estimating the shear wave velocity based on a fitting of the thresholded temporal data and the thresholded spatial data; and (j) generating an output that indicates the estimated shear wave velocity.

19. The method as recited in claim 18, wherein the motion amplitude threshold is based on a percentage of maximum motion in a local region about a particular spatial location.

20. The method as recited in claim 19, wherein the motion amplitude threshold is eighty percent of the maximum motion in the local region about the particular spatial location.

21. The method as recited in claim 18, wherein step (i) includes fitting the thresholded temporal data and the thresholded spatial data using a linear fitting.

22. The method as recited in claim 21, wherein the linear fitting is at least one of random sample consensus (RANSAC) linear fitting, weighted RANSAC linear fitting, least squares linear fitting, or weighted least squares linear fitting.

23. The method as recited in claim 18, wherein step (j) includes computing a mechanical property based on the estimated shear wave velocity and generating the output includes generating an output that indicates the mechanical property.

24. The method as recited in claim 18, wherein the motion profiles include at least one of displacement profiles representing displacement over the plurality of time points, velocity profiles representing velocity over the plurality of time points, or acceleration profiles representing acceleration over the plurality of time points.

25. The method as recited in claim 18, wherein:
step (b) includes spatially averaging multiple motion profiles along a depth direction;
steps (c)-(i) are repeatedly performed using a sliding window that is moved over data points in the motion profiles to estimate shear wave velocity over a two-dimensional area; and
step (j) includes generating a two-dimensional image of shear wave velocity in the two-dimensional area.

26. The method as recited in claim 25, wherein in each repetition the sliding window is centered on a different data point and the sliding window is sized to contain a number of overlapping data points in adjacent applications of the sliding window.

27. The method as recited in claim 25, wherein the sliding window is applied along an x-direction.

28. The method as recited in claim 27, further comprising repeating steps (c)-(i) with a second sliding window that is applied along the depth direction, and wherein step (j) includes generating the two-dimensional image of shear wave velocity as, $$V = \frac{V_x V_z}{\sqrt{V_x^2 + V_z^2}}$$

wherein $V_x$ is the shear wave velocity estimated along the x-direction and $V_z$ is the shear wave velocity estimated along the depth-direction.

29. The method as recited in claim 27, further comprising repeating steps (c)-(i) with a second sliding window that is moved over data points in the motion profiles along a y-direction to estimate shear wave velocity over a three-dimensional area, and wherein step (j) includes generating a three-dimensional image of shear wave velocity.

30. The method as recited in claim 18, wherein steps (c)-(e) are repeatedly performed along small patches of length p, in a spatial window centered on a pixel to obtain estimates of shear wave velocity along a lateral direction and a depth direction at the pixel, and wherein in each repetition the spatial window is moved to another pixel in a two-dimensional area.

31. The method as recited in claim 30, wherein the estimates of shear wave velocity along the lateral direction and along the depth direction are each weighted by a quality metric.

32. The method as recited in claim 31, wherein the quality metric is one of a motion amplitude, a coefficient of determination, or an inlier ratio.

33. The method as recited in claim 18, wherein:
step (b) includes directionally filtering the motion profiles to produce multiple motion fields;
steps (c)-(i) are repeatedly performed using a sliding window that is moved over data points in each of the motion fields to estimate shear wave velocity over a two-dimensional area; and
step (j) includes generating a two-dimensional image of shear wave velocity in the two-dimensional area.

34. The method as recited in claim 33, wherein the estimates of shear wave velocity are averaged together and weighted by a quality metric.

35. The method as recited in claim 34, wherein the quality metric is one of a motion amplitude, a coefficient of determination, or an inlier ratio.

* * * * *